(12) United States Patent
Kawashima et al.

(10) Patent No.: US 6,897,304 B2
(45) Date of Patent: May 24, 2005

(54) CEPHEM COMPOUNDS AND ESBL-DETECTING REAGENTS CONTAINING THE SAME

(75) Inventors: Seiichiro Kawashima, Tokyo (JP);
Keiichi Hiramatsu, Tokyo (JP);
Hideaki Hanaki, Kanagawa (JP);
Hiroaki Yamazaki, Tokyo (JP);
Hidenori Harada, Tokyo (JP)

(73) Assignee: Zenyaku Kogyo Kabushiki Kaisha, Tokyo (JP)

( * ) Notice: Subject to any disclaimer, the term of this patent is extended or adjusted under 35 U.S.C. 154(b) by 43 days.

(21) Appl. No.: 10/380,628
(22) PCT Filed: Sep. 21, 2001
(86) PCT No.: PCT/JP01/08235
§ 371 (c)(1),
(2), (4) Date: Mar. 21, 2003
(87) PCT Pub. No.: WO02/24707
PCT Pub. Date: Mar. 28, 2002

(65) Prior Publication Data
US 2004/0019202 A1 Jan. 29, 2004

(30) Foreign Application Priority Data
Sep. 22, 2000 (JP) .................................. 2000-288719

(51) Int. Cl.⁷ .................... C07D 501/22; C07D 501/24; C12Q 1/34
(52) U.S. Cl. ......................................... 540/222; 435/18
(58) Field of Search ............................ 540/222; 435/18

(56) References Cited
U.S. PATENT DOCUMENTS
5,061,702 A  * 10/1991  Atsumi et al. .............. 540/222

FOREIGN PATENT DOCUMENTS
EP          175610        3/1986
JP       2000-316597     11/2000
JP       2004166694 A  *  6/2004  ............ C12Q/1/34

OTHER PUBLICATIONS

J. Sirot: "Detection of extended–spectrum plasmid–mediated beta–lactamases by disk diffusion" Clin. Microbiol. Infect., vol. 2, suppl. 1, pp. S35–S39.

* cited by examiner

Primary Examiner—Mark L. Berch
(74) Attorney, Agent, or Firm—Oblon, Spivak, McClelland, Maier & Neustadt, P.C.

(57) ABSTRACT

A cephem compound or pharmaceutically acceptable salt thereof represented by the formula I:

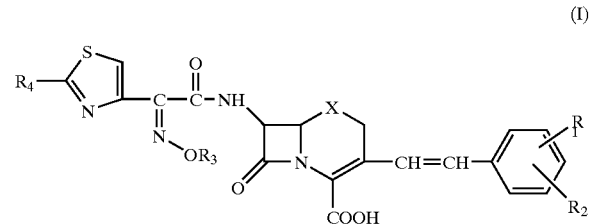

wherein $R_1$ and $R_2$ may be the same or different and each represent hydrogen atom, nitro or cyano; $R_3$ represents $C_1$–$C_6$ alkyl which may be substituted with carboxyl; $R_4$ represents hydrogen atom or amino; X represents —S— or —SO—, there being no case where both of $R_1$ and $R_2$ are simultaneously hydrogen atom.

21 Claims, No Drawings

CEPHEM COMPOUNDS AND ESBL-DETECTING REAGENTS CONTAINING THE SAME

TECHNICAL FIELD

The present invention relates to a novel cephem compound effective for detection of extended-spectrum β-lactamase (ESBL) producing bacteria to which third-generation cephem-related antibiotics are ineffective. More specifically, it relates to a cephem compound or pharmaceutically acceptable salt thereof effective for detection of ESBL-producing bacteria and represented by the formula I:

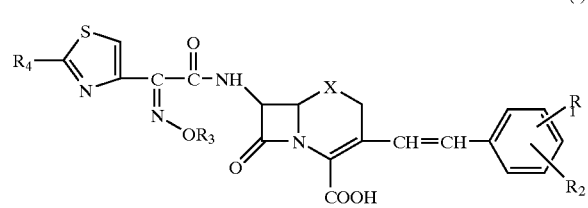

wherein $R_1$ and $R_2$ may be the same or different and each represent hydrogen atom, nitro or cyano; $R_3$ represents $C_1$–$C_6$ alkyl which may be substituted with carboxyl; $R_4$ represents hydrogen atom or amino; X represents —S— or —SO—, there being no case where both of $R_1$ and $R_2$ are simultaneously hydrogen atom.

BACKGROUND ART

Since the middle of 1980s, nosocomial infection through ESBL-producing *Klebsiella pneumoniae* and *Escherichia coli* has been recognized as a serious problem in Europe and then in U.S.A. Recently, such bacteria tend to gradually increase also in Japan.

ESBLs hydrolyze even broad-spectrum third-generation β-lactam antibacterial agents such as cefotaxime (CTX), ceftazidime (CAZ) and aztreonam (AZT) which are stable against conventional type β-lactamases, and have reduced susceptibility to these medical agents. Continued administration of such medical agents against ESBL-producing bacteria not only would be hopeless from the viewpoint of cure but also might harmfully lead to spreading of ESBL-producing bacteria and developing of new resistant bacteria.

Thus, it is necessary to identify ESBL-producing bacteria through rapid and proper testing and to use proper antibiotics.

Currently, ESBL-detecting testing may be conducted, for example, by 1) method for measuring MICs (minimum inhibitory concentrations) to CTX, CAZ, AZT in the presence and absence of clavulanic acid (CVA), 2) double-disk synergy test method using two kinds of disks, one of which is for CVA and the other of which is for either of CTX, CAZ and AZT, a zone of inhibition around each disk being observed, or 3) E-test method using MIC ratios of CAZ alone and of CAZ with CVA.

However, any of these methods requires MIC measurement through medical-agent susceptibility test to determine the presence of ESBL-producing bacteria, which takes several days for isolation and cultivation of bacteria, actually resulting in failure of rapid determination. Under such circumstances, it has been desired to provide a testing procedure which requires no special operations and devices other than culture of organisms and which is shorter in detection than MIC measurement.

Rapid detection of conventional type β-lactamases such as penicillinase (PCase) and cephalosporinase (CEPase) is concerned with decomposed β-lactam ring of substrate and may be conducted, for example, by (1) acidmetry method for grasping pH change in terms of color change of a pH indicator, (2) iodometry method for utilizing color change in starch-iodine reaction as measure, (3) chromogenic method for grasping change in conjugated system in terms of absorption change in direct visible region and (4) UV method for grasping change in conjugated system in terms of absorption change in ultraviolet region; among these methods, the chromogenic method is said to be most easily accessible from the viewpoint of sensitivity and in that no special devices are required for measurement. Actually, products utilizing chromogenic method with substrate being nitrocefin (JP-56-18197B, U.S. Pat. No. 3,830,700 and British Patent 1408391) are commercially available; however, they react with all β-lactamases and there is no hope of their selective application for ESBL-producing bacteria at all.

DISCLOSURE OF THE INVENTION

Under such circumstances, we, the inventors, made devoted researches to synthesis of β-lactam compounds which are selectively decomposed only by ESBLs and therefore can be used for rapid detection of ESBLs, and found that novel β-lactam compounds of the formula I have an ideal characteristic of being substrate detectable under visible light in chromogenic method, thus accomplishing the present invention.

The compounds of the present invention are represented by the formula I shown above. The terms used for definition of letters in this formula will be defined and exemplified in the following.

The term "$C_1$–$C_6$" refers to a group having 1 to 6 carbon atoms unless otherwise indicated.

The "$C_1$–$C_6$ alkyl group" refers to a straight- or branched-chain alkyl group such as methyl, ethyl, n-propyl, isopropyl, n-butyl, tert-butyl, n-pentyl or n-hexyl.

In the compounds I of the present invention, at least one of substituents of $R_1$ and $R_2$ must be nitro or cyano which are electron-withdrawing group so that change in conjugated system may be involved to cause absorption change in visible region upon decomposition of β-lactam ring. Therefore, there is no case where both of $R_1$ and $R_2$ are simultaneously hydrogen atom.

The compounds according to the present invention may be as follows, though the present invention is not limited to these compounds.

7-[2-(2-aminothiazol-4-yl)-2-(1-carboxy-1-methylethoxyimino)acetamido]-3-(2,4-dinitrostyryl)-3-cephem-4-carboxylic acid 7-[2-(2-aminothiazol-4-yl)-2-(1-carboxy-1-methylethoxyimino)acetamido]-3-(2,6-dinitrostyryl)-3-cephem-4-carboxylic acid 7-[2-(2-aminothiazol-4-yl)-2-(1-carboxy-1-methylethoxyimino)acetamido]-3-(4-nitrostyryl)-3-cephem-4-carboxylic acid 7-[2-(2-aminothiazol-4-yl)-2-(1-carboxy-1-methylethoxyimino)acetamido]-3-(2,4-dicyanostyryl)-3-cephem-4-carboxylic acid 7-[2-(2-aminothiazol-4-yl)-2-(1-carboxy-1-methylethoxyimino)acetamido]-3-(4-cyanostyryl)-3-cephem-4-carboxylic acid 7-[2-(2-aminothiazol-4-yl)-2-(1-carboxy-1-methylethoxyimino)acetamido]-3-(2-cyanostyryl)-3-cephem-4-carboxylic acid 7-[2-(1-carboxy-1-methylethoxyimino)-2-(thiazol-4-yl)
acetamido]-3-(2,4-dinitrostyryl)-3-cephem-4-carboxylic
acid 7-[2-(2-aminothiazol-4-yl)-2-(1-carboxy-1-
methylethoxyimino)acetamido]-3-(2,4-dinitrostyryl)-3-
cephem-4-carboxylic acid-1-oxide 7-[2-(2-aminothiazol-4-yl)-2-methoxyiminoacetamido]-3-
(4-nitrostyryl)-3-cephem-4-carboxylic acid 7-[2-(2-aminothiazol-4-yl)-2-methoxyiminoacetamido]-3-
(2,4-dicyanostyryl)-3-cephem-4-carboxylic acid 7-[2-(2-aminothiazol-4-yl)-2-methoxyiminoacetamido]-3-
(2,6-dicyanostyryl)-3-cephem-4-carboxylic acid 7-[2-(2-aminothiazol-4-yl)-2-methoxyiminoacetamido]-3-
(2-cyanostyryl)-3-cephem-4-carboxylic acid 7-[2-(2-aminothiazol-4-yl)-2-
carboxymethoxyiminoacetamido]-3-(2,4-dinitrostyryl)-
3-cephem-4-carboxylic acid 7-[2-(2-aminothiazol-4-yl)-2-
carboxymethoxyiminoacetamido]-3-(2,6-dinitrostyryl)-
3-cephem-4-carboxylic acid 7-[2-(2-aminothiazol-4-yl)-2-
carboxymethoxyiminoacetamido]-3-(4-nitrostyryl)-3-
cephem-4-carboxylic acid 7-[2-(2-aminothiazol-4-yl)-2-
carboxymethoxyiminoacetamido]-3-(2-nitrostyryl)-3-
cephem-4-carboxylic acid 7-[2-(2-aminothiazol-4-yl)-2-
carboxymethoxyiminoacetamido]-3-(2,4-dicyanostyryl)-
3-cephem-4-carboxylic acid 7-[2-(2-aminothiazol-4-yl)-2-
carboxymethoxyiminoacetamido]-4-(4-cyanostyryl)-3-
cephem-4-carboxylic acid 7-[2-(2-aminothiazol-4-yl)-2-
carboxymethoxyiminoacetamido]-4-(2-cyanostyryl)-3-
cephem-4-carboxylic acid 7-[2-carboxymethoxyimino-2-(thiazol-4-yl)acetamido]-3-
(2,4-dinitrostyryl)-3-cephem-4-carboxylic acid 7-[2-(2-aminothiazol-4-yl)-2-
carboxymethoxyiminoacetamido]-3-(2,4-dinitrostyryl)-
3-cephem-4-carboxylic acid-1-oxide Since the compounds of formula I have vinyl group at the 3-position, the following cis isomers (i) and trans isomers (ii) exist, the respective isomers and their mixtures being included in the compounds of the present invention.

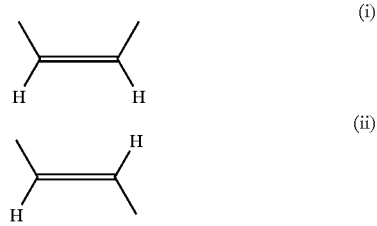

As to the imino group at the 7-position, the following syn isomers (iii) and anti isomers (iv) exist, the respective isomers and their mixtures being included in the compounds of the present invention. The syn isomers are preferable.

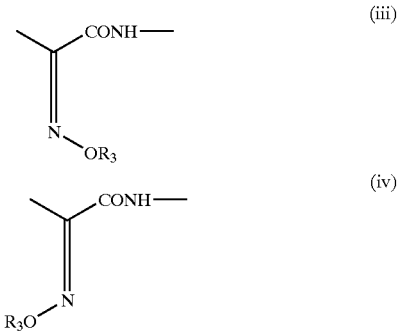

wherein $R_3$ is as defined above.

Moreover, the compounds of the invention may be in the form of pharmaceutically acceptable salts such as alkali salts, organic ammonium salts or acid addition salts. The appropriate alkali salts which can be used include, for example, potassium salt, sodium salt, calcium salt, magnesium salt, barium salt and ammonium salt. The appropriate acid addition salts which can be used include inorganic acid salts such as hydrochloride, hydrobromide, sulfate, nitrate and phosphate as well as organic acid salts such as acetate, oxalate, propionate, glycolate, lactate, pyruvate, malonate, succinate, maleate, fumarate, malate, tartrate, citrate, benzoate, cinnamate, methanesulfonate, benzenesulfonate, p-toluenesulfonate and salicylate.

The compounds of the present invention may be prepared by the following procedure.

The compounds I of the present invention are obtained by removing protective group from a synthetic intermediate (7) in a solvent in the presence of a protecting-group cleaving reagent such as hydrochloric acid, aluminium chloride, formic acid, trifluoroacetic acid, p-toluenesulfonic acid. For example, tetrahydrofuran (THF), dichloromethane, chloroform, benzene, ethyl acetate, dimethylformamide (DMF), acetone or mixture thereof may be used as the solvent. The reaction is effected at the temperature range of ice cooling to room temperature for 1–6 hours, using 1–200 fold mol of the above-mentioned acid per mol of the compound of the formula (7). When trifluoroacetic acid is to be used, it is preferably reacted in the presence of, for example, anisole, thioanisole or phenol so as to accelerate the reaction and suppress any side reaction.

Thus obtained compound of the present invention may be separated and purified as needs demand, according to an ordinary method such as extraction, condensation, neutralization, filtration, recrystallization or column chromatography.

The synthetic intermediate (7) of the present invention may be obtained by a method of the following reaction scheme 1. More specifically, 7-amino-3-chloromethylcephem compound represented by the formula (3) is reacted with 2-aminothiazolcarboxylic acid represented by the formula (4) in a solvent such as dichloromethane, DMF or THF in the presence of a condensing agent such as dicyclohexylcarbodiimide or N,N'-carbonyldiimidazole at the temperature range of −20 to 40° C. for 1–24 hours to thereby obtain the compound represented by the formula (5). Then, the compound of the formula (5) is reacted with sodium iodide and triphenylphosphine in a solvent for 1–6 hours and then with aldehyde of the formula (6) in the presence of base to obtain the compound of the formula (7).

As the solvent, for example, acetone, dichloromethane, a mixture of dichloromethane with water, DMF, THF, benzene or ethyl acetate may be used. As the base, not only an inorganic base such as sodium hydrogen carbonate, sodium carbonate, sodium hydrate, potassium-tert-butoxide, sodiumethoxide or sodiummethoxide but also an organic base such as 1,8-diazabicyclo[5.4.0]-7-undecene (DBU) or 1,5-diazabicyclo[4.3.0]non-5-en (DBN) may be used.

4-dinitrostyryl)-7-(2-thienylacetamido)-3-cephem-4-carboxylic acid] was used as a reference compound.

TEST EXAMPLE 1)

Each of the test compounds is dissolved in dimethyl sulfoxide. Paper disks with a diameter of 8 mm containing

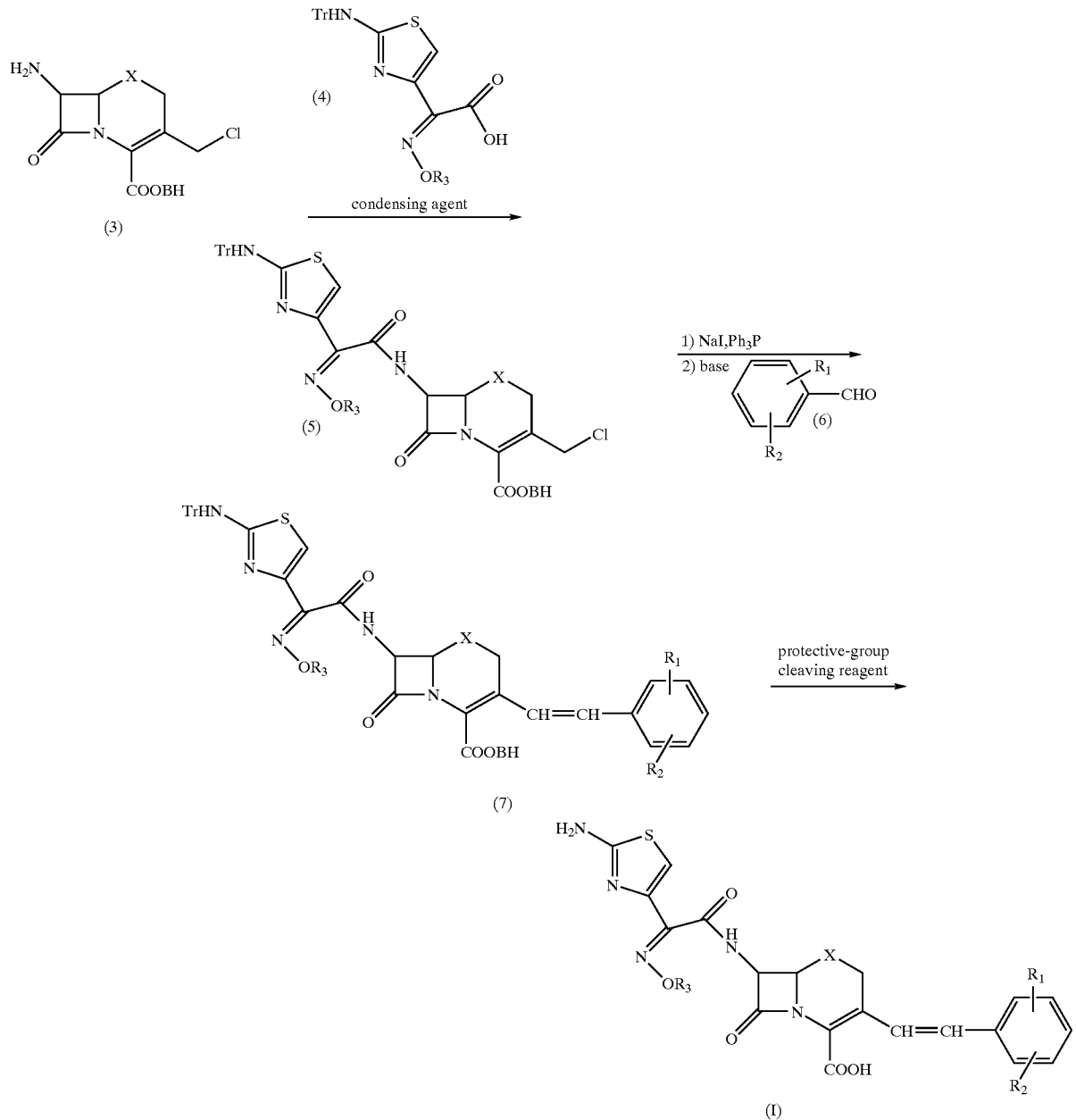

wherein $R_1$, $R_2$, $R_3$ and X are as defined above.

TEST EXAMPLE

Next, reactivity of the compounds of the present invention represented by the formula I against β-lactamases is disclosed to demonstrate its utility as detecting reagents. The numbers of test compounds in the Test Example corresponds to those in Examples referred to hereinafter. A nonspecific reagent on β-lactamase, i.e., nitrocefin [compound A: 3-(2, the test compounds in an amount of 5 or 25 μg per disk were prepared and dried in air. Each of these disks was added dropwise with a solution of β-lactamases (50 μl) prepared to a concentration of 1 U/ml with distilled water and allowed for 10 minutes. Then, color changes were observed to demonstrate reactivities of the respective test compounds against β-lactamases as shown TABLE 1 below.

TABLE 1

Reactivity against β-lactamases

| test compound | content (μg/disk) | PCase | CEPase | ESBL | color change |
|---|---|---|---|---|---|
| compound 1 | 5 | − | − | ++ | pale yellow → red |
| compound 2 | 5 | − | − | + | pale yellow → orange |
| compound 3 | 25 | − | − | + | pale yellow → golden yellow |
| compound 4 | 5 | − | − | ++ | pale yellow → orange |
| compound 5 | 5 | − | − | ++ | pale yellow → red |
| compound 6 | 5 | − | − | ++ | pale yellow → orange |
| compound A | 5 | ++ | ++ | ++ | pale yellow → red |

−: negative
+: positive
++: highly positive

PCase is an enzyme isolated from *B. cereus* (production of Sigma Chemical Co. :PCase Type I); and CEPase, from *E. cloacae* (production of Sigma chemical Co. :CEPase Type IV).

As is clear from the above results of TABLE 1, the compounds of the present invention did not react with PCase and CEPase which are conventional β-lactamases, and reacted with ESBL in a short period with color being changed from pale yellow to between golden yellow to red so that they were found to be effective for selective detection of ESBL which has been impossible in the case of the reference compound which are conventional β-lactamases detecting reagents.

It was confirmed that the compounds I of the present invention had the similar results against PCase-, CEPase- or ESBL-producing bacteria; their application as ESBL-producing bacteria detecting reagents is much prospective.

When the compounds I of the present invention are used as ESBL-producing bacteria detecting reagents, not only cultured and isolated bacteria but also cultured bacteria from phlegmatic specimen may suffice as samples for detection.

When the compounds of the present invention are used as ESBL-detecting reagents, the presence of ESBL may be rapidly detected by adding dropwise a culture solution of bacteria (5–10 μl) to a white or pale disk of absorptive cellulose such as filter paper or dextran impregnated with the compound of the present invention dissolved in a solvent such as N,N-dimethylformamide or dimethyl sulfoxide; color change 10 minutes after or 30 minutes after at longest of the dropping can be observed to readily determine the presence or absence of ESBL. In this respect, color change into deep color such as red or orange is preferable since the color of the compounds of the present invention before the reaction is pale yellow.

The compounds of the present invention, which are characteristic in color development in a short period due to decomposition of β-lactam ring and usable for determination with no necessity of optical measurement devices such as UV-VIS spectrophotometer, can be utilized as simple and rapid detecting reagents for ESBLs.

Furthermore, to standardize concentration of detecting reagents and incubation time period for samples for detection will enable quantitative measurement.

BEST MODE FOR CARRYING OUT THE INVENTION

The present invention will be more specifically illustrated with reference to the following examples. It is to be, however, noted that the present invention is not limited to these.

Example 1

Preparation of 7-[2-(2-aminothiazol-4-yl)-2-(1-carboxy-1-methylethoxyimino)acetamido]-3-(2,4-dinitrostyryl)-3-cephem-4-carboxylic acid (compound 1)

(1) 7-[2-(1-Methyl-1-tert-butoxycarbonylethoxyimino)-2-(2-tritylaminothiazol-4-yl)acetamido]-3-chloromethyl-3-cephem-4-carboxylic acid benzhydryl ester (940 mg, 0.97 mmol) dissolved in acetone (10 ml) and added with sodium iodide (145.4 mg, 0.97 mmol) and triphenylphosphine (254.4 mg, 0.97 mmol) was stirred at room temperature for 1 hour. The reaction mixture was condensed under reduced pressure to an extent that acetone was reduced to half. Then, the reaction mixture was added with dichloromethane (10 ml), water (10 ml), 2,4-dinitrobenzaldehyde (760.9 mg, 3.88 mmol) and sodium hydrogen carbonate (244.4 mg, 2.91 mmol) and stirred at room temperature overnight.

Dichloromethane layer was removed and water layer was extracted with dichloromethane (20 ml) and combined with the last dichloromethane layer and dried over magnesium sulfate. The filtered filtrate was added with Wako Gel™ C-200 (10 g) and the solvent was removed under reduced pressure for adsorption and chromatographed by dry column chromatography filled with Wako Gel™ C-200. Impurities were removed with 400 ml of hexane-ethyl acetate (4:1) and the targeted object was eluted with hexane-ethyl acetate (1:1). The solvent was removed under reduced pressure and the residue was crystallized with hexane-ether (1:1) to obtain 730 mg (yield: 67.7%) of 7-[2-(1-methyl-1-tert-butoxycarbonylethoxyimino)-2-(2-tritylaminothiazol-4-yl)acetamido]-3-(2,4-dinitrostyryl)-3-cephem-4-carboxylic acid benzhydryl ester as orange color powder.

The NMR spectrum indicated that this specimen was Z-isomer.

1H-NMR (CDCl$_3$) δ: 1.36 (3H, s), 1.37 (3H, s), 1.41 (9H, s), 2.92 (1H, d, J=18.3 Hz), 3.27 (1H, d, J=18.3 Hz), 5.04 (1H, d, J=5.0 Hz), 6.05 (1H, dd, J=8.6 Hz, 5.0 Hz), 6.70 (1H, s), 6.80 (1H, d, J=13.0 Hz), 6.84 (1H, d, J=13.0 Hz), 6.89 (1H, br), 6.93 (1H, s), 7.2–7.4 (25H, m), 7.47 (1H, d, J=8.6 Hz), 8.19 (1H, d, J=8.6 Hz), 8.29 (1H, dd, J=8.6 Hz, 2.3 Hz), 8.85 (1H, d, J=2.3 Hz)

(2) A mixture of the obtained compound (500 mg, 0.45 mmol) with anisole (1 ml, 9.0 mmol) was added dropwise with trifluoro acetic acid (5.2 ml, 67.5 mmol) under ice-water cooling, and stirred at the temperature for 2.5 hours. The reaction mixture was added with isopropyl ether (50 ml) and the resulting precipitate was filtered out, washed with isopropyl ether and dried to obtain 160 mg (yield: 46.7%) of the titled compound as yellow powder.

The NMR spectrum indicated that this specimen was E-isomer.

1H-NMR (DMSO-d$_6$) δ: 1.48 (3H, s), 1.49 (3H, s), 3.75 (1H, d, J=17.5 Hz), 4.09 (1H, d, J=17.5 Hz), 5.30 (1H, d, J=5.0 Hz), 5.90 (1H, dd, J=8.2 Hz, 5.0 Hz), 6.78 (1H, s), 7.17 (1H, d, J=16.5 Hz), 7.60 (1H, d, J=16.5 Hz), 7.70 (2H, d, J=8.7 Hz), 8.23 (2H, d, J=8.7 Hz) 9.52 (1H, d, J=8.2 Hz)

Example 2

Preparation of 7-[2-(2-aminothiazol-4-yl)-2-(1-carboxy-1-methylethoxyimino)acetamido]-3-(4-nitrostyryl)-3-cephem-4-carboxylic acid (compound 2)

(1) 7-[2-(1-methyl-1-tert-butoxycarbonylethoxyimino)-2-(2-tritylaminothiazol-4-yl)acetamido]-3-chloromethyl-3- cephem-4-carboxylic acid benzhydryl ester (775 mg, 0.8 mmol), sodium iodide (120 mg, 0.8 mmol), triphenylphosphine (210 mg, 0.8 mmol), 4-nitrobenzaldehyde (483 mg, 3.2 mmol) and sodium hydrogen carbonate (200 mg, 2.4 mmol) were used to conduct the procedure similar to that shown in (1) of Example 1 to obtain 568 mg (yield: 66%) of 7-[2-(1-methyl-1-tert-butoxycarbonylethoxyimino)-2-(2-tritylaminothiazol-4-yl)acetamido]-3-(4-nitrostyryl)-3-cephem-4-carboxylic acid benzhydryl ester as yellow powder.

The NMR spectrum indicated that this specimen was a mixture of Z- and E-isomers (ca 3:1).

1H-NMR (CDCl$_3$) δ:
(Z-isomer)
1.43 (9H, s), 1.61 (3H, s), 1.63 (3H, s), 3.11 (1H, d, J=18.3 Hz), 3.32 (1H, d, J=18.3 Hz), 5.08 (1H, d, J=5.1 Hz) 6.09 (1H, dd, J=8.7 Hz, 5.1 Hz), 6.58 (1H, d, J=12.2 Hz), 6.65 (1H, d, J=12.2 Hz), 6.73 (1H, s), 6.88 (1H, br), 6.92 (1H, s), 7.2–7.5 (27H, m), 8.14 (1H, d, J=8.6 Hz), 8.27 (1H, d, J=8.7 Hz)
(E-isomer)
1.41 (9H, s), 1.60 (6H, s), 3.64 (1H, d, J=17.5 Hz), 3.77 (1H, d, J=17.5 Hz), 5.14 (1H, d, J=5.1 Hz), 6.04 (1H, dd, J=8.7 Hz, 5.1 Hz), 6.74 (1H, d, J=16.3 Hz), 6.75 (1H, s), 6.73 (1H, s), 6.88 (H, br), 6.92 (1H, s), 7.2–7.5 (27H, m), 8.14 (1H, d, J=8.6 Hz), 8.27 (1H, d, J=8.7 Hz)

(2) The obtained compound (400 mg, 0.38 mmol), anisole (1 ml, 9.0 mmol) and trifluoro acetic acid (5 ml) were used to conduct the procedure similar to that shown in (2) of the Example 1 to obtain 175 mg (yield: 65%) of the titled compound as yellow powder.

The NMR spectrum indicated that this specimen was a mixture of Z- and E-isomers (ca 3:1).

1H-NMR (DMSO-d$_6$) δ:
(Z-isomer)
1.43 (3H, s), 1.47 (3H, s), 3.16 (1H, d, J=17.5 Hz), 3.59 (1H, d, J=17.5 Hz), 5.31 (1H, d, J=5.0 Hz), 5.86 (1H, dd, J=8.1 Hz, 5.0 Hz), 6.66 (1H, d, J=12.2 Hz), 6.72 (1H, d, J=12.2 Hz), 6.77 (1H, s), 7.52 (2H, d, J=8.7 Hz), 8.16 (2H, d, J=8.7 Hz), 9.45 (1H, d, J=8.1 Hz)
(E-isomer)
1.48 (3H, s), 1.49 (3H, s), 3.75 (1H, d, J=17.5 Hz), 4.09 (1H, d, J=17.5 Hz), 5.30 (1H, d, J=5.0 Hz), 5.90 (1H, dd, J=8.2 Hz, 5.0 Hz), 6.78 (1H, s), 7.17 (1H, d, J=16.5 Hz), 7.60 (1H, d, J=16.5 Hz), 7.70 (2H, d, J=8.7 Hz), 8.23 (2H, d, J=8.7 Hz), 9.52 (1H, d, J=8.2 Hz)

Example 3

Preparation of 7-[2-(2-aminothiazol-4-yl)-2-(1-carboxy-1-methylethoxyimino)acetamido]-3-(4-cyanostyryl)-3-cephem-4-carboxylic acid (compound 3)

(1) 7-[2-(1-methyl-1-tert-butoxycarbonylethoxyimino)-2-(2-tritylaminothiazol-4-yl)acetamido]-3-chloromethyl-3-cephem-4-carboxylic acid benzhydryl ester (775 mg, 0.8 mmol), sodium iodide (120 mg, 0.8 mmol), triphenylphosphine (210 mg, 0.8 mmol), 4-cyanobenzaldehyde (428 mg, 3.2 mmol) and sodium hydrogen carbonate (200 mg, 2.4 mmol) were used to conduct the procedure similar to that shown in (1) of Example 1 to obtain 464 mg (yield: 55%) of 7-[2-(1-methyl-1-tert-butoxycarbonylethoxyimino)-2-(2-tritylaminothiazol-4-yl)acetamido]-3-(4-cyanostyryl)-3-cephem-4-carboxylic acid benzhydryl ester as cream color powder.

The NMR spectrum indicated that this specimen was a mixture of Z- and E-isomers (ca 1:1).

1H-NMR (CDCl$_3$) δ:
(Z-isomer)
1.43 (9H, s), 1.60 (6H, s), 3.10 (1H, d, J=18.1 Hz), 3.30 (1H, d, J=18.1 Hz), 5.08 (1H, d, J=5.0 Hz), 6.0–6.1 (1H, m), 6.57 (2H, d×2, J=12.2 Hz), 6.73 (1H, s), 6.89 (1H, br), 6.92 (1H, s), 7.2–7.6 (29H, m), 8.18 (1H, d, J=8.7 Hz)
(E-isomer)
1.41 (9H, s), 1.61 (6H, s), 3.63 (1H, d, J=17.5 Hz), 3.75 (1H, d, J=17.5 Hz), 5.14 (1H, d, J=5.0 Hz), 6.0–6.1 (1H, m), 6.75 (1H, s), 6.89 (1H, br), 7.07 (1H, s), 7.2–7.6 (31H, m), 8.25 (1H, d, J=8.7 Hz)

(2) This compound (398 mg, 0.38 mmol), anisole (1 ml, 9.0 mmol) and trifluoro acetic acid (5 ml, 67.5 mmol) were used to conduct the procedure similar to that shown in (2) of Example 1 to obtain 154 mg (yield: 58%) of the titled compound as cream color powder.

The NMR spectrum indicated that this specimen was a mixture of Z- and E-isomers (1:1).

Example 4

Preparation of 7-[2-(2-aminothiazol-4-yl)-2-methoxyiminoacetamido]-3-(4-nitrostyryl)-3-cephem-4-carboxylic acid (compound 4)

(1) 7-[2-methoxyimino-2-(2-tritylaminothiazol-4-yl)acetamido]-3-chloromethyl-3-cephem-4-carboxylic acid benzhydryl ester (395 mg, 0.47 mmol), sodium iodide (70 mg, 0.47 mmol), triphenylphosphine (123 mg, 0.47 mmol), 4-nitrobenzaldehyde (284 mg, 1.88 mmol) and sodium hydrogen carbonate (120 mg, 1.4 mmol) were used to conduct the procedure similar to that shown in (1) of Example 1 to obtain 242 mg (yield: 55%) of 7-[2-methoxyimino-2-(2-tritylaminothiazol-4-yl)acetamido]-3-(4-nitrostyryl)-3-cephem-4-carboxylic acid benzhydryl ester as yellow powder.

The NMR spectrum indicated that this specimen was a mixture of Z- and E-isomers (ca 2:1).

1H-NMR(CDCl$_3$) δ:
(Z-isomer) 3.12 (1H, d, J=18.3 Hz), 3.35 (1H, d, J=18.3 Hz), 4.07 (3H, s), 5.09 (1H, d, J=4.9 Hz), 5.9–6.0 (1H, m), 6.62 (2H, d×2, J=12.0 Hz), 6.74 (1H, s), 6.79 (1H, d, J=8.9 Hz), 6.93 (1H, s), 7.02 (1H, br), 7.2–7.5 (27H, m), 8.16 (2H, d, J=8.9 Hz)
(E-isomer)
3.66 (1H, d, J=17.5 Hz), 3.79 (1H, d, J=17.5 Hz), 4.09 (3H, s), 5.15 (1H, d, J=5.0 Hz), 5.9–6.0 (1H, m), 6.75 (1H, d, J=16.3 Hz), 6.76 (1H, s), 6.88 (1H, d, J=8.6 Hz), 7.09 (1H, s), 7.2–7.5 (27H, m), 7.53 (1H, d, J=16.3 Hz), 8.10 (1H, d, J=8.9 Hz)

(2) This compound (210 mg, 0.22 mmol), anisole (0.5 ml, 4.5 mmol) and trifluoro acetic acid (2.5 ml, 33.8 mmol) were used to conduct the procedure similar to that shown in (2) of Example 1 to obtain 100 mg (yield: 70%) of the titled compound as yellow powder.

The NMR spectrum indicated that this specimen was a mixture of Z- and E-isomers (ca 2:1).

1H-NMR (DMSO-d$_6$) δ:
(Z-isomer)
3.18 (1H, d, J=17.8 Hz), 3.57 (1H, d, J=17.8 Hz), 3.87 (1H, s), 5.28 (1H, d, J=4.8 Hz), 5.82 (1H, dd, J=8.2 Hz, 4.8 Hz), 6.69 (2H, d×2, J=12.0 Hz), 6.79 (1H, s), 7.52 (2H, d, J=8.7 Hz), 8.16 (2H, d, J=8.7 Hz), 9.65 (1H, d, J=8.2 Hz)
(E-isomer)
3.75 (1H, d, J=17.0 Hz), 4.05 (1H, d, J=17.0 Hz), 3.89 (1H, s), 5.28 (1H, d, J=4.8 Hz), 5.82 (1H, dd, J=8.2 Hz, 4.8 Hz), 6.60-6.75 (2H, d×2, J=12.0 Hz), 6.80 (1H, s), 7.16 (1H, d, J=16.3 Hz), 7.61 (1H, d, J=16.3 Hz), 7.70 (2H, d, J=8.7 Hz), 8.23 (2H, d, J=8.7 Hz), 9.71 (1H, d, J=8.2 Hz)

Example 5

Preparation of 7-[2-(2-aminothiazol-4-yl)-2-carboxymethoxyiminoacetamido]-3-(2,4-dinitrostyryl)-3-cephem-4-carboxylic acid (compound 5)

(1) 7-[2-tert-butoxycarbonylmethoxyimino-2-(2-tritylaminothiazol-4-yl)acetamido]-3-chloromethyl-3-cephem-4-carboxylic acid benzhydryl ester (500 mg, 0.53 mmol), 2,4-dinitrobenzaldehyde (416 mg, 2.12 mmol), sodium iodide (79.4 mg, 0.53 mmol), triphenylphosphine (139 mg, 0.53 mmol) and sodium hydrogen carbonate (133.6 mg, 1.59 mmol) were used to conduct the procedure similar to that shown in (1) of Example 1 to obtain 350 mg (yield: 61%) of 7-[2-carboxymethoxyimino-2-(2-tritylaminothiazol-4-yl)acetamido]-3-(2,4-dinitrostyryl)-3-cephem-4-carboxylic acid benzhydryl ester as yellow powder.

The NMR spectrum indicated that this specimen was Z-isomer.

1H-NMR (CDCl$_3$) δ:

1.42 (9H, s), 2.94 (1H, d, J=18.1 Hz), 3.23 (1H, d, J=18.1 Hz), 4.73 (2H, s), 5.04 (1H, d, J=5.0 Hz), 5.93 (1H, dd, J=7.9 Hz, 5.0 Hz), 6.77 (1H, s), 6.82 (2H, s), 6.92 (1H, s), 6.99 (1H, br), 7.2–7.4 (25H, m), 7.50 (1H, d, J=8.7 Hz), 8.31 (1H, dd, J=8.7 Hz, 2.3 Hz), 8.56 (1H, d, J=7.9 Hz), 8.85 (1H, d, J=2.3 Hz)

(2) This compound (238 mg, 0.22 mmol), anisole (0.5 ml, 4.5 mmol) and trifluoro acetic acid (2.5 ml, 33.8 mmol) were used to conduct the procedure similar to that shown in (2) of Example 1 to obtain 120 mg (yield: 73%) of the titled compound as yellow powder.

The NMR spectrum indicated that this specimen was E-isomer.

1H-NMR (DMSO-d$_6$) δ:

3.75 (1H, d, J=17.6 Hz), 4.00 (1H, d, J=17.6 Hz), 4.63 (2H, s), 5.30 (1H, d, J=4.8 Hz), 5.90 (1H, dd, J=8.1 Hz, 4.8 Hz), 6.86 (1H, s), 7.26 (1H, d, J=16.0 Hz), 7.56 (1H, d, J=16.0 Hz), 8.00 (1H, d, J=8.7 Hz), 8.51 (1H, dd, J=8.7 Hz, 2.3 Hz), 8.74 (1H, d, J=2.3 Hz), 9.64 (1H, d, J=8.1 Hz)

Example 6

Preparation of 7-[2-(2-aminothiazol-4-yl)-2-carboxymethoxyiminoacetamido]-3-(4-nitrostyryl)-3-cephem-4-carboxylic acid (compound 6)

(1) 7-[2-tert-butoxycarbonylmethoxyimino-2-(2-tritylaminothiazol-4-yl)acetamido]-3-chloromethyl-3-cephem-4-carboxylic acid benzhydryl ester (470 mg, 0.5 mmol), sodium iodide (75 mg, 0.5 mmol), triphenylphosphine (131 mg, 0.5 mmol), 4-nitrobenzaldehyde (302 mg, 2 mmol) and sodium hydrogen carbonate (126 mg, 1.5 mmol) were used to conduct the procedure similar to that shown in (1) of Example 1 to obtain 260 mg (yield: 50%) of 7-[2-carboxymethoxyimino-2-(2-tritylaminothiazol-4-yl)acetamido]-3-(4-nitrostyryl)-3-cephem-4-carboxylic acid benzhydryl ester as yellow powder.

The NMR spectrum indicated that this specimen was a mixture of Z- and E-isomers (ca 2:1).

1H-NMR (CDCl$_3$) δ:
(Z-isomer)

1.44 (9H, s), 3.12 (1H, d, J=18.3 Hz), 3.29 (1H, d, J=18.3 Hz), 4.76 (2H, s), 5.09 (1H, d, J=5.0 Hz), 5.98 (1H, dd, J=8.3 Hz, 5.0 Hz), 6.58 (1H, d, J=12.0 Hz), 6.65 (1H, d, J=12.0 Hz), 6.80 (1H, s), 6.91 (1H, s), 7.00 (1H, br), 7.2–7.5 (27H, m), 8.15 (2H, d, J=8.7 Hz), 8.66 (2H, d, J=8.3 Hz)
(E-isomer)

1.42 (9H, s), 3.63 (1H, d, J=17.2 Hz), 3.76 (1H, d, J=17.2 Hz) 4.78 (2H, s), 5.15 (1H, d, J=5.0 Hz), 5.92 (1H, dd, J=8.3 Hz, 5.0 Hz), 6.74 (1H, d, J=16.3 Hz), 6.83 (1H, s), 7.00 (1H, br) 7.07 (1H, s), 7.2–7.5 (27H, m), 7.51 (1H, d, J=16.3 Hz), 8.10 (2H, d, J=8.7 Hz), 8.79 (2H, d, J=8.3 Hz)

(2) This compound (257 mg, 0.25 mmol), anisole (0.5 ml, 4.5 mmol) and trifluoro acetic acid (2.5 ml, 33.8 mmol) were used to conduct the procedure similar to that shown in (2) in Example 1 to obtain 126 mg (yield: 73%) of the titled compound as yellow powder.

The NMR spectrum indicated that this specimen was a mixture of Z- and E-isomers (ca 2:1).

1H-NMR (DMSO-d$_6$) δ:
(Z-isomer)

3.19 (1H, d, J=18.0 Hz), 3.59 (1H, d, J=18.0 Hz), 4.61 (1H, s), 5.29 (1H, d, J=5.0 Hz), 5.84 (1H, dd, J=8.3 Hz, 5.0 Hz), 6.60-6.75 (2H, d×2, J=12.0 Hz), 6.83 (1H, s), 7.51 (2H, d, J=8.9 Hz) 8.16 (2H, d, J=8.9 Hz), 9.57 (1H, d, J=8.3 Hz)
(E-isomer)

3.75 (1H, d, J=17.2 Hz), 4.06 (1H, d, J=17.2 Hz), 4.62 (1H, s), 5.29 (1H, d, J=5.0 Hz), 5.54 (1H, dd, J=8.6 Hz, 5.0 Hz), 6.85 (2H, s), 7.16 (1H, d, J=16.3 Hz), 7.61 (1H, d, J=16.3 Hz), 7.70 (2H, d, J=8.9 Hz), 8.23 (2H, d, J=8.9 Hz), 9.62 (1H, d, J=8.6 Hz)

CAPABILITY OF EXPLOITATION IN INDUSTRY

The cephem compounds according to the present invention, which can develop color in a short period due to decomposition of β-lactam ring, can be used for selective detection of ESBLs with no necessity of optical measurement devices such as UV-VIS spectrophotometer and therefore can be utilized as simple and rapid detecting reagents for ESBLs. Moreover, to standardize concentration of detecting reagents and incubation time period for samples for detection will enable quantitative measurement.

What is claimed is:

1. Cephem compound or pharmaceutically acceptable salt thereof represented by the formula I (I)

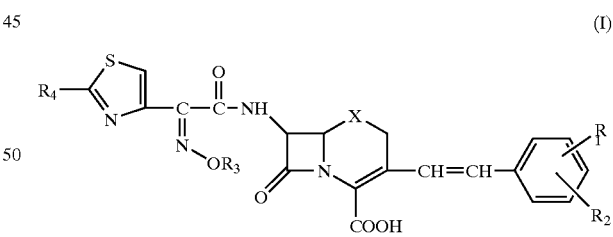

wherein $R_1$ and $R_2$ may be the same or different and each represent hydrogen atom, nitro or cyano; $R_3$ represents $C_1$–$C_6$ alkyl which may be substituted with carboxyl; $R_4$ represents hydrogen atom or amino; X represents —S— or —SO—, there being no case where both of $R_1$ and $R_2$ are simultaneously hydrogen atom.

2. The compound according to claim 1 wherein X is —S—.

3. The compound according to claim 1 wherein $R_3$ is methyl which may be substituted with carboxyl, or propyl substituted with carboxyl.

4. The compound according to claim 1 wherein $R_4$ is amino.

5. The compound according to claim 1 wherein X is —S— and $R_3$ is methyl which may be substituted with carboxyl, or propyl substituted with carboxyl and $R_4$ is amino.

6. The compound according to claim 1 wherein the compound represented by the formula I is 7-[2-(2-aminothiazol-4-yl)-2-(1-carboxy-1-methylethoxyimino)acetamido]-3-(2,4-dinitrostyryl)-3-cephem-4-carboxylic acid, 7-[2-(2-aminothiazol-4-yl)-2-(1-carboxy-1-methylethoxyimino)acetamido]-3-(4-nitrostyryl)-3-cephem-4-carboxylic acid, 7-[2-(2-aminothiazol-4-yl)-2-(1-carboxy-1-methylethoxyimino)acetamido]-3-(4-cyanostyryl)-3-cephem-4-carboxylic acid, 7-[2-(2-aminothiazol-4-yl)-2-methoxyiminoacetamido]-3-(4-nitrostyryl)-3-cephem-4-carboxylic acid, 7-[2-(2-aminothiazol-4-yl)-2-carboxymethoxyiminoacetamido]-3-(2,4-dinitrostyryl)-3-cephem-4-carboxylic acid or 7-[2-(2-aminothiazol-4-yl)-2-carboxymethoxyiminoacetamido]-3-(4-nitrostyryl)-3-cephem-4-carboxylic acid.

7. The compound according to claim 1 wherein the compound represented by the formula I is 7-[2-(2-aminothiazol-4-yl)-2-(1-carboxy-1-methylethoxyimino)acetamido]-3-(2,4-dinitrostyryl)-3-cephem-4-carboxylic acid.

8. The compound according to claim 1 wherein the compound represented by the formula I is 7-[2-(2-aminothiazol-4-yl)-2-carboxymethoxyiminoacetamido]-3-(2,4-dinitrostyryl)-3-cephem-4-carboxylic acid.

9. An extended-spectrum β-lactamase (ESBL) detecting reagent which is a disk of absorptive cellulose impregnated with a compound as claimed in claim 1 as a coloring agent.

10. The cephem compound or pharmaceutically acceptable salt thereof of claim 1, wherein the cephem compound is a Z-isomer.

11. The cephem compound or pharmaceutically acceptable salt thereof of claim 1, wherein the cephem compound.

12. The cephem compound or pharmaceutically acceptable salt thereof of claim 1, which is a mixture of Z- and E-isomers.

13. The cephem compound or pharmaceutically acceptable salt thereof of claim 1, wherein the imino group is a syn isomer.

14. The cephem compound or pharmaceutically acceptable salt thereof of claim 1, which is a pharmaceutically acceptable salt of at least one of a hydrochloride, hydrobromide, sulfate, nitrate, phosphate, acetate, oxalate, propionate, glycolate, lactate, pyruvate, malonate, succinate, maleate, fumarate, malate, tartrate, citrate, benzoate, cinnamate, methanesulfonate, benzenesulforiate, p-tolunesulfonate or salicylate.

15. The cephem compound or pharmaceutically acceptable salt thereof of claim 1, which has been purified with at least one method selected from the group consisting of extraction, condensation, neutralization, filtration, recrystallization or column chromatography.

16. A method for detecting an extended-spectrum β-lactamase producing bacteria, comprising:

contacting a composition with the cephem compound of claim 1 to determine a color change.

17. The method of claim 16, wherein the composition is a solution of a bacteria culture.

18. The method of claim 16, wherein contacting includes adding a culture solution of bacteria to an absorptive cellulose impregnated with the cephem compound of claim 1.

19. The method according to claim 16, wherein the cephem compound is at least one of 7-[2-(2-aminothiazol-4-yl)-2-(1-carboxy-1-methylethoxyimino)acetamido]-3-(2,4-dinitrostyryl)-3-cephem-4-carboxylic acid, 7-[2-(2-aminothiazol-4-yl)-2-(1-carboxy-1-methylethoxyimino)acetamido]-3-(4-nitrostyryl)-3-cephem-4-carboxylic acid, 7-[2-(2-aminothiazol-4-yl)-2-(1-carboxy-1-methylethoxyimino)acetamido]-3-(4-cyanostyryl)-3-cephem-4-carboxylic acid, 7-[2-(2-aminothiazol-4-yl)-2-methoxyiminoacetamido]-3-(4-nitrostyryl)-3-cephem-4-carboxylic acid, 7-[2-(2-aminothiazol-4-yl)-2-carboxymethoxyiminoacetamido]-3-(2,4-dinitrostryryl)-3-cephem-4-carboxylic acid or 7-[2-(2-aminothiazol-4-yl)-2-carboxymethoxyiminoacetamido]-3-(4-nitrostyryl)-3-cephem-4-carboxylic acid.

20. The method according to claim 16, wherein the cephem compound is 7-[2-(2-aminothiazol-4-yl)-2-(1-carboxy-1-methylethoxyimino)acetamido]-3-(2,4-dinitrostyryl)-3-cephem-4-carboxylic acid.

21. The method according to claim 16, wherein the cephem compound is 7-[2-(2-aminothiazol-4-yl)-2-carboxymethoxyiminoacetamido]-3-(2,4-dinitrostyryl)-3-cephem-4-carboxylic acid.

* * * * *